United States Patent [19]

Schmidt et al.

[11] Patent Number: 4,990,716
[45] Date of Patent: Feb. 5, 1991

[54] PREPARATION OF DIPHENYLMETHANES

[75] Inventors: Gregory F. Schmidt; Paul D. Williams, both of Midland, Mich.

[73] Assignee: The Dow Chemical Company, Midland, Mich.

[21] Appl. No.: 364,730

[22] Filed: Jun. 9, 1989

[51] Int. Cl.$^5$ .................................................. C07C 2/02
[52] U.S. Cl. ...................................... 585/426; 585/458
[58] Field of Search .................................. 585/426, 458

[56] References Cited

U.S. PATENT DOCUMENTS

| 2,526,896 | 10/1950 | Ipatieff et al. . |
| 2,557,505 | 6/1951 | Ipatieff et al. . |
| 2,671,815 | 3/1954 | Pines et al. . |
| 2,954,412 | 9/1960 | Wulf et al. . |
| 3,978,144 | 8/1976 | Eilingsfeld et al. . |
| 4,022,847 | 5/1977 | McClure . |
| 4,038,213 | 7/1977 | McClure et al. . |
| 4,041,090 | 8/1977 | McClure . |
| 4,117,019 | 9/1978 | Eilingsfeld et al. . |
| 4,197,417 | 4/1980 | Morley . |
| 4,288,646 | 9/1981 | Olah . |
| 4,289,918 | 9/1981 | Sato et al. . |
| 4,303,551 | 12/1981 | Vaughan . |
| 4,304,724 | 12/1981 | Nutt . |
| 4,304,949 | 12/1981 | Zweig et al. . |
| 4,316,997 | 2/1982 | Vaughan . |
| 4,317,949 | 3/1982 | Vaughan . |
| 4,339,621 | 7/1982 | Morley . |
| 4,446,329 | 5/1984 | Waller . |
| 4,547,604 | 10/1985 | Olah . |
| 4,585,750 | 4/1986 | Farcasiu . |
| 4,661,411 | 4/1987 | Martin et al. . |
| 4,683,216 | 7/1987 | Farcasiu . |
| 4,791,081 | 12/1988 | Childress et al. . |

Primary Examiner—Curtis R. Davis

[57] ABSTRACT

Diphenylmethanes such as o-benzyltoluene are prepared by contacting a benzyl halide with a benzene in the presence of a catalytic amount of a normally solid, insoluble perfluorosulfonic acid polymer under reaction conditions. The o-benzyltoluenes are useful intermediates in the production of anthraquinone and anthracene.

7 Claims, No Drawings

PREPARATION OF DIPHENYLMETHANES

BACKGROUND OF THE INVENTION

This invention relates to processes for the preparation of diphenylmethanes including diphenylmethane and alkyl-substituted diphenylmethanes.

Diphenylmethanes are useful intermediates in the preparation of anthraquinone, anthracene and other fused ring compounds. The diphenylmethanes have been prepared by the reaction of chloro-methylbenzenes, e.g., benzyl chloride, with benzene or substituted benzenes such as toluene in the presence of a dehydrohalogenation catalyst such as aluminum chloride, copper chromite, hydrofluoric acid and sulfuric acid. See, for example, U.S. Pat. Nos. 4,117,019; 4,339,621 and 4,304,949. Unfortunately, most of such processes yield unwanted by-products which are difficult to separate from the desired diphenylmethanes. Processes employing sulfuric acid or similar liquid acid catalyst yield a liquid product mixture wherein it is expensive to separate the desired diphenylmethane from the catalyst and other components of the product mixture. Furthermore, when sulfuric acid is used as the catalyst, it is often necessary to employ a substantial excess of the benzene reactant in order to inhibit unwanted sulfonation of the resultant product.

In view of the deficiencies of the aforementioned prior art processes, it is highly desirable to provide a new process for making diphenylmethanes in a product mixture from which the diphenylmethanes can be separated in high yield and high purity using simple distillation.

SUMMARY OF THE INVENTION

The present invention is such a process which comprises contacting a benzyl halide with a benzene in the presence of a catalytic amount of a normally solid, insoluble perfluorosulfonic acid polymer under conditions sufficient to form a diphenylmethane. Surprisingly, the practice of this process yields the diphenylmethane in selectivities as high or higher than are achievable using conventional liquid acid catalysts: yet the desired diphenylmethane can be removed from the catalyst by simple physical separation. In the production of o-benzyltoluenes by the reaction of an o-xylyl halide with a benzene, it is particularly surprising that the desired o-benzyltoluene is produced to the substantial exclusion of dimers and trimers of the o-xylyl halide.

The diphenylmethanes produced by this process are generally useful as solvents for a variety of organic compounds. The o-benzyltoluenes which are most advantageously produced by the process are particularly useful as intermediates in the production of anthraquinone and anthracene.

DETAILED DESCRIPTION OF THE INVENTION

The benzyl halides suitably employed in the practice of this invention include aromatic compounds having a halomethyl moiety bonded to a benzene ring. In addition to the halomethyl moiety, the benzene ring is optionally bonded to one or more other monovalent organic substituents such as alkyl, alkoxy, halo and other organic substituents which are inert under the reaction conditions of the process. Preferred benzyl halides are those represented by the formula:

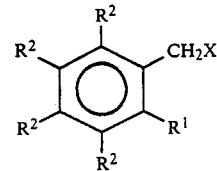

wherein $R^1$ is hydrogen or alkyl having from 1 to 4 carbons, more preferably methyl, and each $R^2$ is independently hydrogen or halo such as chloro and bromo, more preferably hydrogen. Examples of preferred benzyl halides include o-xylyl chloride, 3-chloro-2-chloromethyl-toluene, 4-chloro-2-chloromethyl-toluene, 5-chloro-2-chloromethyl-toluene, 6-chloro-2-chloromethyl-toluene, 6-bromo-2-chloromethyl-toluene, 4-bromo-2-chloromethyl-toluene, 3-bromo-2-chloromethyl-toluene, 5-bromo-2-chloromethyl-toluene, and corresponding bromomethyl compounds. Of these benzyl halides the o-xylyl halides such as o-xylyl chloride and o-xylyl bromide are especially preferred with o-xylyl chloride being the most preferred.

Benzenes which are suitably used in the process of this invention are aromatic compounds having a benzene ring to which is optionally bonded up to 5 monovalent organic substituents which are inert under the reaction conditions of the process. Preferred benzenes are those represented by the formula:

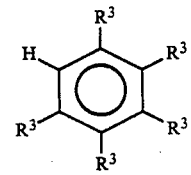

wherein each $R^3$ is independently hydrogen, alkyl, aryl, alkoxy, halo, haloaryl, and the like. Examples of preferred benzenes include benzene, toluene, o-xylene, m-xylene, p-xylene, biphenyl, 1,4-diphenylbenzene, 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, pentamethylbenzene, chlorobenzene, bromobenzene, o-chlorotoluene, m-chlorotoluene, p-chlorotoluene, 4-bromo-1-ethylbenzene, t-butylbenzene, and 4,4'-dichlorobiphenyl. Of these benzenes, benzene and toluene are more preferred, with benzene being the most preferred.

The perfluorosulfonic acid polymers employed to catalyze the reactive process of this invention have structures that include a substantially fluorinated carbon chain that has attached to it side chains that are also substantially fluorinated and contain sulfonic acid groups or derivatives of sulfonic acid groups. The sulfonic acid groups may be neutralized with metals such as iron, zinc, aluminum, copper and the like. Preferred perfluorosulfonic acid polymers are represented by the following structural formula:

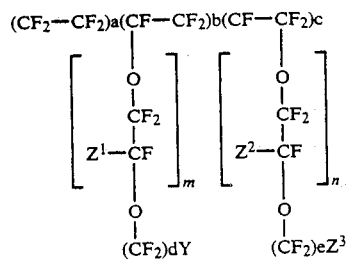

wherein:

Y is SO₃H, or any group easily converted to SO₃H;
each $Z^1$, $Z^2$, and $Z^3$ is independently F, Cl, Br, CF₃, CF₂Cl, or fluorinated alkyl;
the ratio of a/b varies from about 2 to about 50:
c is 0 or greater than 0:
m and n are independently 0 to 4: and
d and e are independently 2 to 5.

Of these polymers represented by the foregoing formula, most preferred are those wherein Y is SO₃H, the ratio of a to b is from 4 to 10, c is 0, m is 0 and d is 2. The perfluorosulfonic acid polymers including methods for their preparation are described in greater detail in U.S. Pat. No. 4,791,081 which is hereby incorporated by reference in its entirety.

The perfluorosulfonic acid polymer is employed as all or a part of a heterogeneous catalyst composition which can be physically separated from the liquid mixture produced by the process. Accordingly, the polymer is normally solid under the conditions of the process and is insoluble in the reaction mixture used in the process. While the polymer can be employed neat, it is preferred to use it deposited as a thin layer on a solid support or carrier. The catalyst is preferably used in the form of a finely divided, porous solid, more preferably one having an average particle diameter in the range from about 0.1 to about 15 millimeters, an average pore diameter in the range from about 1 to about 100 micrometers and a surface area in the range from about 0.001 to about 20 square meters/gram. The chemical composition of the carrier or support employed is not particularly critical. Examples of suitable supports include alumina, silica, zeolites, silicon carbide, silica-alumina, porous glass, ceramic, spinel, clay or carbon. An exemplary method for depositing the polymer on a solid support is described in U.S. Pat. No. 4,661,411, which is hereby incorporated by reference in its entirety.

In practicing the process of this invention in a batchwise manner, it is generally desirable to charge a reactor with a benzyl halide and a benzene in proportions suitable to provide acceptable yields of the desired diphenylmethane. Preferably the molar ratio of the benzyl halide to the benzene is in the range from about 1:5 to about 1:1000 most preferably from about 1:10 to about 1:100 Although not required, it is sometimes desirable to employ a liquid organic solvent for the reactants, usually in an amount of from about 1 to about 100 volumes of solvent per volume of reactants.

The reactants and solvent, if any, are then thoroughly mixed and the heterogeneous catalyst is then added to the mixture. The catalyst is added in an amount which is sufficient to catalyze the desired reaction. Preferably this amount is in the range from about 0.0001 to about 0.01, most preferably from about 0 001 to about 0.005, weight percent of catalyst based on the total weight of the reactants.

The process of the invention can be effectively practiced in a continuous manner by continuously passing the reactants in either a liquid or gaseous phase through a bed or column of the catalyst. Due to the physical properties of the reactants and products and the chemistry of the reaction, it is preferred to employ a distillation column reactor similar to that described in U.S. Pat. No. 4,709,115 for carrying out the reaction. As a result of using such a reactor, it is possible to improve conversion and selectivity to the desired diphenylmethane over that achieved with conventional reactors which are typically used in continuous reactions. The residence time for the reactants to remain in contact with the catalyst is that which is sufficient to permit acceptable conversion to the desired diphenylmethane, preferably a residence time from about 0.01 to about 10 minutes. Unreacted starting materials can be recycled to the reactor in a conventional manner.

In either the continuous or batchwise manner, the process is suitably practiced in air or under an atmosphere of an inert gas such as nitrogen. The pressure employed is not critical and is preferably in the range from about 1 to about 50 atmospheres. The temperature used in the process is suitably any which will permit the reaction to proceed at a reasonable rate to form the desired diphenylmethane and is preferably in the range from about 140° C. to about 220° C., most preferably from about 175° C. to about 185° C.

The desired diphenylmethane product is preferably recovered by physically separating the liquid product from the solid heterogeneous catalyst using any conventional procedure for separating a liquid from a solid, e.g., filtration.

For the purposes of this invention, the term "diphenyl methane" means a compound having two phenyl groups or substituted phenyl groups bonded to a methane carbon or a substituted methane carbon. Preferably the diphenylmethane is represented by the formula:

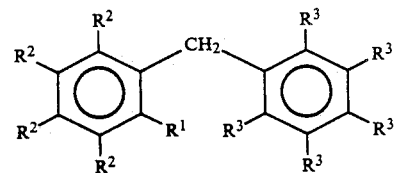

wherein $R^1$, $R^2$ and $R^3$ are as previously defined. Especially preferred are the o-benzyltoluenes which are represented by the formula:

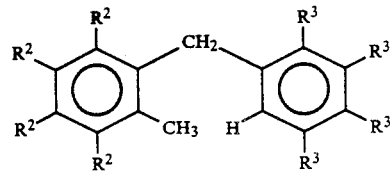

wherein $R^2$ and $R^3$ are as previously defined. In the practice of the process of the invention, the limiting reactant, usually the benzyl halide, is converted in amounts greater than 90 percent to the desired diphenylmethane, usually o-benzyltoluene. Preferably the conversion is greater than 95 percent with selectivities to the diphenylmethane being greater than 92 percent. The o-benzyltoluenes are valuable starting materials for the production of anthracene, anthraquinone and their derivatives. Anthraquinone is conveniently produced by oxidizing the o-benzyltoluene in the presence of heterocatalyst and then cyclizing as described in Japanese Kokai No.:1984-36636. Anthracene and its derivatives are readily prepared by thermal reaction of gaseous o-benzyl toluene as described in U.S. Pat. No. 3,801,661.

ILLUSTRATIVE EMBODIMENTS

The following examples are given to illustrate the invention and should not be interpreted as limiting it in any way. Unless stated otherwise, all parts and percentages are given by weight.

EXAMPLE 1

Into a 600-mL Hastelloy° C Parr reactor equipped with a mechanical stirrer and operating at a temperature of 140° C. are charged 350 mL of benzene and 50 mL of o-xylyl chloride. To the reactor is then added a 5-g portion of perfluorosulfonic acid polymer deposited on an alumina carrier (average particle diameter of 1.6 mm, average pore size of 8 μm and a surface area of 0.25 m²/g) which is prepared by the procedure described in Example 1 of U.S. Pat. No. 4,791,081. The reactor is then closed to the atmosphere and heated to 140° C. and maintained at that temperature for 4 hours while mechanically stirring the reactants and the catalyst. The contents of the reactor are then filtered to separate the catalyst from the liquid reaction product. Analysis of the reaction product indicates that 64 percent of the o-xylyl chloride is converted to o-benzyltoluene in selectivity of 93 percent. The o-benzyltoluene is separated from the reaction product mixture by simple distillation.

EXAMPLE 2

The reactor used in Example 1 is charged with 300 mL of benzene and 4 g of the catalyst used in Example 1. The reactor contents are then heated with stirring to 140° C. A 50-mL portion of benzene and 4 mL of xylyl chloride are then mixed together in a separate vessel at ambient conditions and transferred under nitrogen to the reactor at 140° C. Analysis of the reaction mixture after 12 minutes by gas chromatography indicates that 99 percent of the xylyl chloride is converted in selectivity of 93 percent to o-benzyltoluene.

EXAMPLE 3

The procedure of Example 2 is followed except that the temperature of the reactor contents is maintained at 185° C. Analysis of the reaction mixture after 3 minutes indicates conversion of more than 99 percent of the xylyl chloride with selectivity to o-benzyltoluene of 93 percent.

What is claimed is:

1. A process for producing a diphenylmethane which comprises contacting o-xylyl halide with benzene or toluene in the presence of a catalytic amount of a normally solid, insoluble perfluorosulfonic acid polymer represented by the formula:

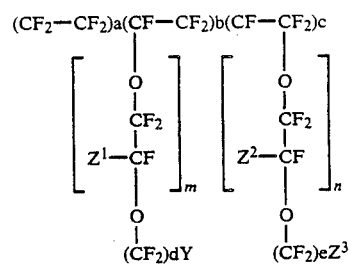

wherein:
Y is SO₃H, or any group convertible to SO₃H;
each $Z^1$, $Z^2$, and $Z^3$ is independently F, Cl, Br, CF₃, CF₂Cl, or fluorinated alkyl;
the ratio of a/b varies from about 2 to about 50:
c is 0 or greater than 0:
m and n are independently 0 to 4: and
d and e are independently 2 to 5.

2. The process of claim 1 wherein the diphenylmethane is o-benzyl toluene.

3. The process of claim 1 wherein the polymer is deposited on a finely divided, porous solid, having an average particle diameter in the range from about 0.1 to about 15 millimeters, an average pore diameter in the range from about 1 to about 100 micrometers and a surface area in the range from about 0.001 to about 20 square meters/gram.

4. The process of claim 1 which is carried out in a continuous manner in a distillation column reactor.

5. The process of claim 1 wherein the conditions are as follows: pressure in the range from about 1 to about 50 atmospheres and temperature in the range from about 140° C. to about 220° C.

6. The process of claim 1 wherein the conversion of the o-xylyl halide to the diphenylmethane is greater than 90 percent.

7. The process of claim 6 wherein the conversion of the o-xylyl halide is greater than 95 percent and the selectivity to o-benzyl toluene is greater than 92 percent.

* * * * *

UNITED STATES PATENT AND TRADEMARK OFFICE
CERTIFICATE OF CORRECTION

PATENT NO. : 4,900,716

DATED : February 13, 1990

INVENTOR(S) : Fujita et al

It is certified that error appears in the above-identified patent and that said Letters Patent is hereby corrected as shown below:

Column 7, line 9, Claim 2, change "complete" to -- completed --.

Column 8, line 41, Claim 14, change "p-r" to -- p+r --.

Column 8, line 43, Claim 14, change "bi" to -- Bi --.

Signed and Sealed this

Nineteenth Day of February, 1991

Attest:

HARRY F. MANBECK, JR.

*Attesting Officer*      *Commissioner of Patents and Trademarks*